(12) United States Patent
Plishka

(10) Patent No.: US 7,018,343 B2
(45) Date of Patent: Mar. 28, 2006

(54) BIOPSY NEEDLE AND BIOPSY DEVICE CONTAINING THE SAME

(75) Inventor: Michael Plishka, Northbrook, IL (US)

(73) Assignee: Allegiance Corporation, McGaw Park, IL (US)

( * ) Notice: Subject to any disclaimer, the term of this patent is extended or adjusted under 35 U.S.C. 154(b) by 0 days.

(21) Appl. No.: 10/400,611

(22) Filed: Mar. 27, 2003

(65) Prior Publication Data

US 2003/0212343 A1 Nov. 13, 2003

Related U.S. Application Data

(60) Provisional application No. 60/370,270, filed on Apr. 5, 2002.

(51) Int. Cl.
*A61B 5/10* (2006.01)

(52) U.S. Cl. .................. 600/564; 600/567; 606/167; 606/170

(58) Field of Classification Search ................ 600/564, 600/566, 567; 606/167, 170, 67, 184, 185; 408/228
See application file for complete search history.

(56) References Cited

U.S. PATENT DOCUMENTS

| | | | | |
|---|---|---|---|---|
| 4,157,714 A | * | 6/1979 | Foltz et al. ............... 606/72 |
| 4,561,445 A | * | 12/1985 | Berke et al. ............. 600/372 |
| 4,655,226 A | | 4/1987 | Lee | |
| 4,815,476 A | | 3/1989 | Clossick | |
| 4,961,430 A | | 10/1990 | Sheahon | |
| 4,976,269 A | * | 12/1990 | Mehl ......................... 600/567 |
| 5,052,402 A | | 10/1991 | Bencini et al. | |
| 5,094,247 A | | 3/1992 | Hernandez et al. | |
| 5,100,430 A | | 3/1992 | Avellanet et al. | |
| 5,172,700 A | | 12/1992 | Bencini et al. | |
| 5,238,002 A | | 8/1993 | Devlin et al. | |
| 5,313,958 A | * | 5/1994 | Bauer ....................... 600/567 |
| 5,458,112 A | | 10/1995 | Weaver | |
| 5,651,372 A | | 7/1997 | Caillouette | |
| 5,807,275 A | | 9/1998 | Jamshidi .................. 600/567 |
| 5,810,744 A | | 9/1998 | Chu et al. ................ 600/567 |
| 5,833,668 A | | 11/1998 | Aguilar .................... 604/227 |
| 5,902,278 A | | 5/1999 | Aguilar .................... 604/227 |
| 5,971,940 A | | 10/1999 | Baker et al. ............. 600/567 |
| 6,083,150 A | | 7/2000 | Aznoian et al. .......... 600/56 |
| 6,129,740 A | | 10/2000 | Michelson ............... 606/205 |
| 6,149,607 A | | 11/2000 | Simpson et al. ......... 600/567 |
| 6,176,823 B1 | | 1/2001 | Foley et al. ............. 600/114 |
| 6,450,973 B1 | * | 9/2002 | Murphy ................... 600/564 |
| 2003/0109801 A1 | * | 6/2003 | Rhad et al. .............. 600/564 |

* cited by examiner

*Primary Examiner*—Charles Marmor
*Assistant Examiner*—Sadaf Toor
(74) *Attorney, Agent, or Firm*—Andrew G. Rozycki

(57) ABSTRACT

The invention described herein relates to an improved biopsy needle which enhances the accuracy of the sampling procedure and minimizes the trauma caused by the procedure. The biopsy needle comprises a tip that reduces or minimizes undesirable bias of the needle during sampling penetration of the tissue, the tip comprising a plurality of facets arranged and oriented in a manner which improves the interaction between the needle and tissue during its advancement and penetration therein thereby improving the performance of the biopsy needle. The invention also includes a biopsy device comprising the biopsy needle of the invention.

9 Claims, 10 Drawing Sheets

BIOPSY NEEDLE AND BIOPSY DEVICE CONTAINING THE SAME

RELATED APPLICATION DATA

This application is based on provisional application Ser. No. 60/370,270 filed on Apr. 5, 2002.

FIELD OF THE INVENTION

The invention herein relates to the field of biopsy devices for obtaining tissue samples. In particular, the invention relates to an improved biopsy needle structure.

BACKGROUND OF THE INVENTION

A variety of biopsy devices having sampling needles as part of their structure are available in the medical field. Typical biopsy devices include those that are designed to obtain samples from hard tissues, such as bone, and those that are designed for sampling of softer tissues. Soft tissue biopsy devices can include a structure whereby a sampling needle resides within an outer cannula and moves relative thereto during sampling. In particular, the operation of the device involves extending the distal end of the sampling needle beyond the distal end of the outer cannula to expose and introduce a portion of the needle to the tissue sampling site. A typical structure of a biopsy needle includes a sampling notch located proximal to the distal tip of the needle. The notch is configured to capture and house the sample once it is severed from the surrounding tissue. Subsequent to the capture of the tissue, the outer cannula is advanced in the distal direction over the notch of the needle to sever, trap and retain the sample during withdrawal of the device from the patient.

Soft tissue biopsy devices include manual, automatic and semi-automatic biopsy devices, which permit varying degrees of control over the biopsy procedure by the user. These devices can contain the mechanical elements to operate in a controlled rapid "firing" manner in which the tissue is penetrated by the sampling needle at a very high velocity. Such biopsy devices are described in Bauer U.S. Pat. No. 5,951,489, Bauer U.S. Pat. No. 5,916,175, Bauer U.S. Pat. No. 5,313,958, and Chu et al. U.S. Pat. No. 5,989,196.

Since the biopsy needle is a critical component in such rapidly-firing devices, the structure of the needle and its effect on sampling precision and the resulting trauma are important considerations. In addition to various notch designs, various tip configurations have also been explored. Beveled tips of biopsy needles having sampling notches are also known. One such beveled tip and sampling notch is described in Terwilliger U.S. Pat. No. 5,499,001. Another beveled tip configuration is present on the needle component of a Temno® II biopsy device available from Cardinal Health, Inc. (McGaw Park, Ill.).

There is a need in the medical device field for an improved biopsy needle for sampling soft tissues that possesses increased accuracy and maintains its structural integrity during its operation in biopsy procedures, such as when used in association with biopsy devices employing high velocity needle advancement. Particularly advantageous would be a biopsy needle for use in biopsy devices which, by virtue of its features, reduces or minimizes the amount of trauma to the patient during its use.

SUMMARY OF THE INVENTION

The invention relates to an improved biopsy needle for use in biopsy devices. The needle of the invention, although referred to herein as a biopsy needle, can be used in a variety of devices that advance needles into soft materials. The invention, however, is particularly useful as a component in biopsy devices adapted for obtaining samples from softer tissues utilizing rapid firing mechanisms. It has been discovered that a biopsy needle can be structured with a tip configuration that enhances the accuracy and precision of the needle as it advances at high velocities in a linear direction by reducing the likelihood of bending (deflection) during tissue penetration. It has further been discovered that such performance of the biopsy needle can be yet even further enhanced by coordinating the orientation and position of the sampling notch of the needle relative to the needle tip geometry. One advantage associated with the biopsy needle of the invention is that it permits the use of shorter notch-to-tip lengths while maintaining effective tip sharpness. The combined advantages of the invention include a relatively reduced penetration force required, enhanced accuracy and precision of sampling, reduced likelihood of bending or biasing (deflection), and shortened notch-to-tip lengths—all of which contribute toward reducing or minimizing patient trauma. As a result of the invention, the performance of the biopsy needle of the invention can be significantly improved by virtue of structural and functional attributes of the needle itself, as distinguished from improving the performance of the biopsy device firing mechanisms.

The invention provides a biopsy needle for use in soft tissue sampling procedures comprising an elongated needle body having a longitudinal axis and sharp distal tip having a plurality of facets, wherein each individual facet is substantially planar and four of the facets are arranged such that: each of a first pair of facets is positioned on the opposite side of the needle from the other, and both of said substantially planar surfaces of the facets are oriented in a converging direction toward the distal-most end of the sharp tip; each of a second pair of facets is positioned such that at least a portion of the edge of each facet is positioned between each of said first pair of facets, and at least a portion of both of the second pair of facets distally converge with one another so as to form a shared edge substantially in alignment with the longitudinal axis of the needle and positioned between the distal-most points of each of said first pair of facets.

In a preferred embodiment, the open face of the sampling notch is located proximal to the needle tip and has a surface that is in generally perpendicular orientation relative to the cross-sectional plane intersecting both facets of the first pair of facets. In other words, the intact portion of the needle in the sampling notch region has a longitudinal axis running along the exterior surface of the intact portion that is generally aligned with the cross-sectional plane which separates each facet of the first pair of facets from one another.

The invention also provides for a biopsy device containing, as one of its components, the biopsy needle of the invention.

BRIEF DESCRIPTION OF THE DRAWINGS

FIG. 10A shows the outer cannula partially covering the sampling notch of the biopsy needle, and FIG. 10B shows the outer cannula completely covering the sampling notch of the biopsy needle.

DETAILED DESCRIPTION OF THE INVENTION

As used herein, the phrase "substantially planar" in the context of facet surface is meant to describe a flattened surface circumscribed by definable edges along its perimeter. The term "tip configuration" as used herein is meant to refer to the collective geometry of the facets of the needle tip as part of the biopsy needle structure. The term "biopsy" used to refer to a device or needle, is meant to refer to the interaction of such device or needle with a relatively soft biological material. The advantages of the needle tip configuration of the invention itself can be applied to penetration into soft non-biological materials as well.

Figure 1:
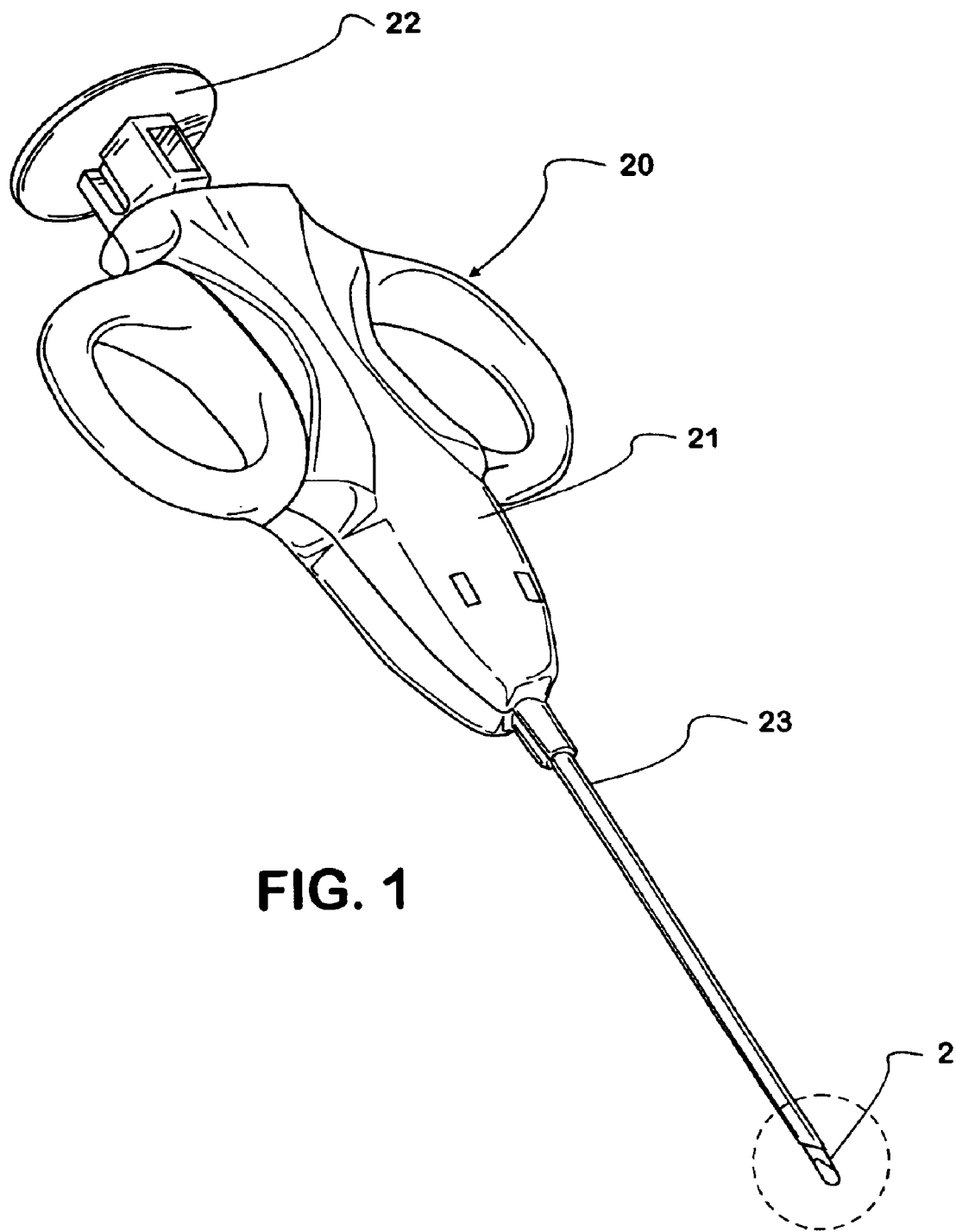
FIG. 1 is an angled side view perspective of a biopsy device comprising the biopsy needle according to one embodiment of the invention.

The biopsy needle of the invention can be utilized in a variety of medical devices that obtain soft tissue samples. Nevertheless, the full extent of the operational advantages of the biopsy needle of the invention are realized when the biopsy needle is employed as a component in a biopsy device (or other medical device) which involves the rapid or high velocity penetration of the biopsy needle into tissue. FIG. 1 depicts a biopsy device 20 having a rapid firing mechanism within (not shown), which can include typical components that can be found in such devices, such as a handle portion 21 housing the operative mechanism components (not shown), loading and trigger component 22, outer cannula 23 and biopsy needle 2 partially residing within the outer cannula 23 with the distal end portion of the needle 2 exposed. Such biopsy devices can contain parts, e.g., the handle portion and loading and trigger component, composed of conventional materials, such as plastic or metallic materials. Preferably, the portion(s) which actually penetrate the tissue as part of a procedure using the device are composed of metal, such as medical grade stainless steel.

Figure 2:
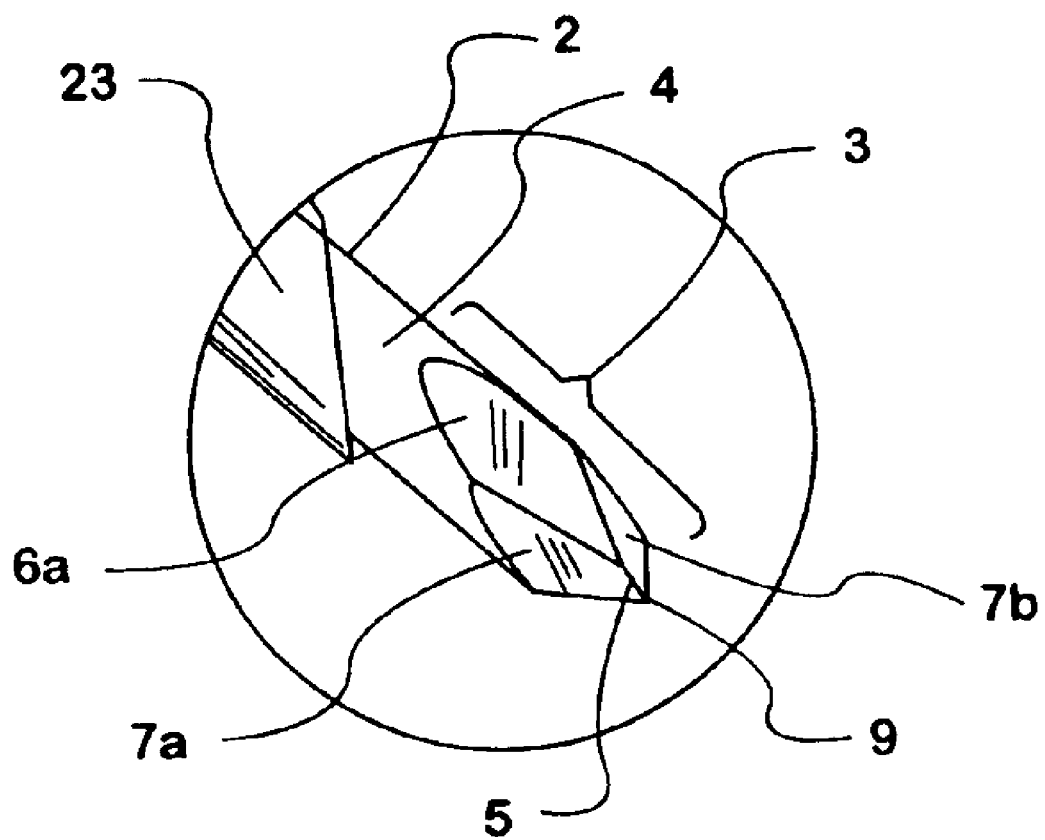
FIG. 2 is an enlarged view of the distal end of the biopsy device depicted in FIG. 1 and tip configuration according to one embodiment of the invention.
Figure 6:
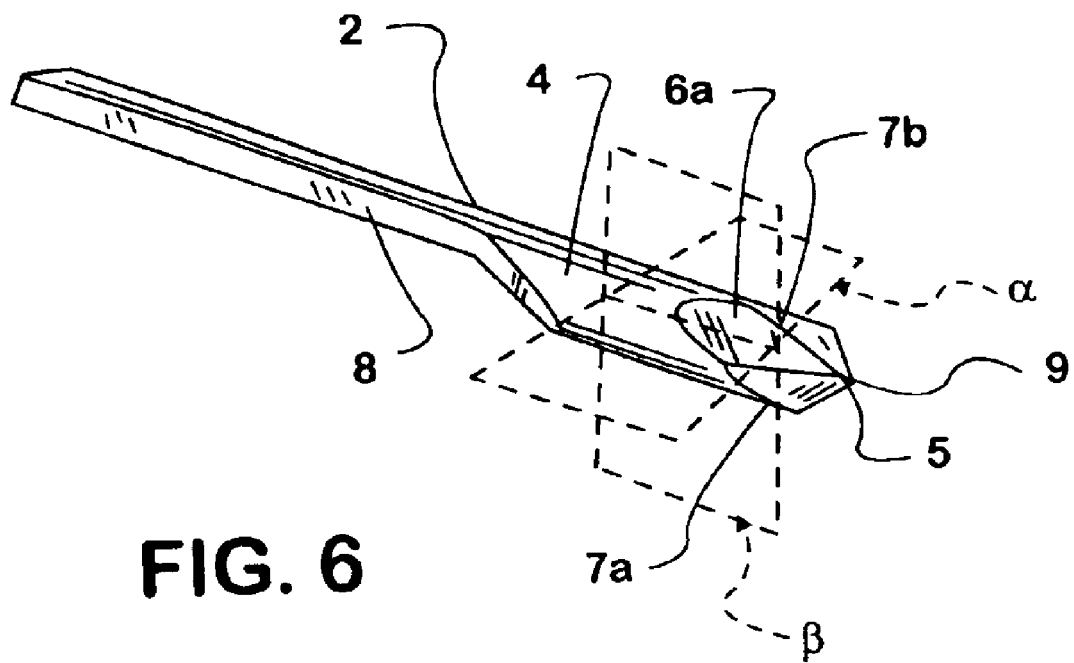
FIG. 6 is an angled side view of the distal end of a biopsy needle and tip configuration according to one embodiment of the invention.

An enlarged detail view of the distal end of the biopsy device and distal end 3 of the needle according to the invention is shown in FIG. 2. Thus, the needle 2 of the invention comprises an elongate needle body 4 having a longitudinal axis and a sharp distal end 3. The needle body shape can be cylindrical (as shown in the firugres), but variations in shape are possible provided they do not interfere with the operational advantages of the invention. The biopsy needle itself is preferably structured for rapid firing mechanisms used in soft tissue biopsy procedures. In general, the needle body 4 can have suitable dimensions (e.g., diameter or gauge, length) for its employment as a component of a biopsy device. Variations on the overall dimensions the biopsy needle are possible, and can be determined in accordance with the nature d/or location of the tissue to be sampled. Referring now to FIG. 6, a larger portion of the biopsy needle itself of the invention is shown. A sampling notch 8 is located proximal relative to the distal end 3 of the biopsy needle. In a typical biopsy device construction, the biopsy needle 2 is positioned within an outer cannula 23. Thus, the movement of the biopsy needle 2 and outer cannula 23 (as shown in FIG. 2) relative to o another functions to sever a tissue sample (not shown) that has encroached into th sampling notch 8 from the tissue sampling site.

Figure 3:
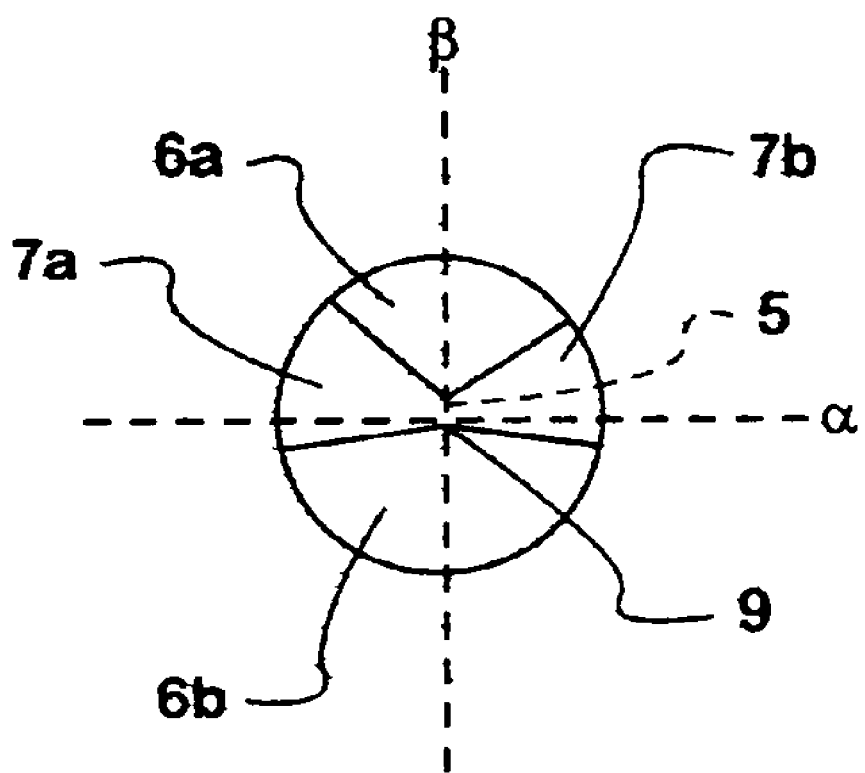
FIG. 3 is a front view of the distal tip of the biopsy needle and tip configuration according to one embodiment of the invention.
Figure 4:
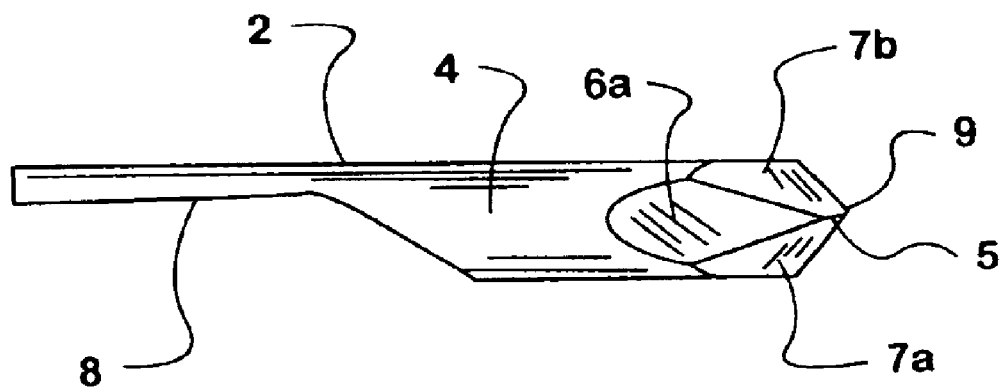
FIG. 4 is a top view of the distal end of the biopsy needle and tip configuration according to one embodiment of the invention.
Figure 5:
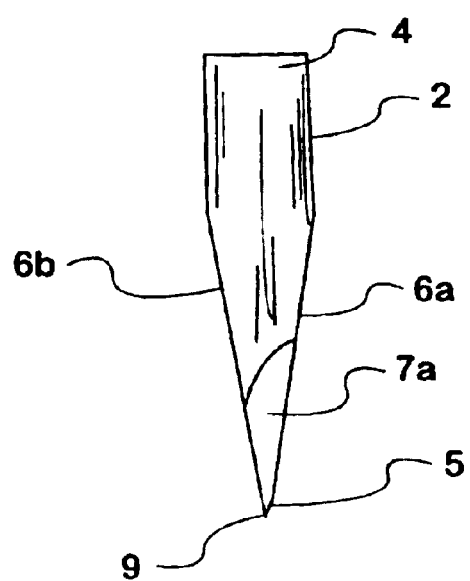
FIG. 5 is a side view of the distal end of the biopsy needle and tip configuration according to one embodiment of the invention.

Referring now to FIGS. 2, 3,4 and 5, the sharp distal end of the biopsy needle 2 comprises four facets arranged in proximity to the distal-most needle point 9. The four facets are described herein as two pair of facets, a first pair of facets 6a and 6b on opposing sides of the needle, and a second pair of facets 7a and 7b, each located between each of the first pair of facets. The interrelationship of the facets to one another and the interaction of the tip to the forces associated with tissue penetration are critical to the invention. Accordingly, the facets are arranged such that the tip configuration comprises two pairs of corresponding facets, specifically referred to as the first pair (facets 6a and 6b) and the second pair (facets 7a and 7b) of facets. The facets 6a and 6b of the first pair are positioned generally on opposite sides of the needle body 4. Each of facets 6a, 6b, 7a and 7b of both pairs comprise a substantially planar surface. Referring now to FIG. 5, the planar surfaces of the first pair of facets 6a and 6b are oriented in a converging direction toward the distal-most point 9 of the distal end 3 of the needle. Although aligned in a converging direction, the two planes do not physically intersect at the distal end 3 as a result of the positioning of the second pair of facets 7a and 7b.

As can be seen from FIGS. 3, 4 and 6, each of the second pair of facets 7a and 7b are positioned generally on opposite regions of the needle body 4 such that the planes of each facet surface 7a and 7b intersect to form a shared edge 5, which is itself in general alignment with the longitudinal axis of the needle body 4. Accordingly, each facet 7a and 7b of the second pair is positioned between each facet 6a and 6b of the first pair. Thus, the remaining portion of both of the second pair of facets 7a and 7b distally intersect or converge with one another along the shared edge 5, and the distal most point 9 of the needle is formed by the uniting of facets 7a, 7b and 6b.

Figure 7:
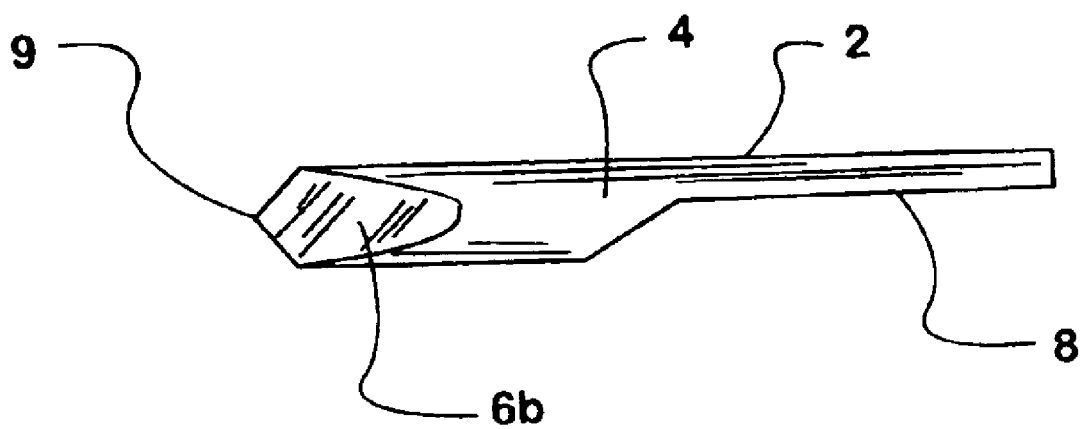
FIG. 7 is a bottom view, and opposing side to, the top view shown in FIG. 4 of the distal end of the biopsy needle according to one embodiment of the invention.
Figure 8A:
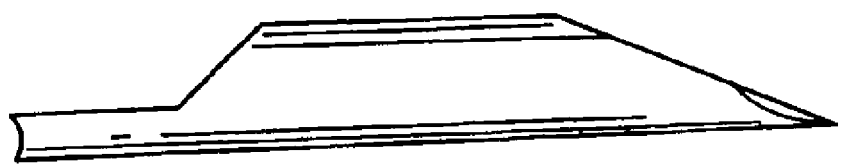
FIGS. 8A and 8B are a side view and an angled side view, respectively, of the distal end of a prior art biopsy needle Temno™ I, to which the biopsy needle of the invention is compared in the examples.

Another aspect of the invention is the alignment or positioning of the sampling notch in relation to the needle tip configuration. Referring now to FIGS. 6 and 7, and in a preferred embodiment, the open face of the sampling notch is located proximal to the needle tip and has a generally perpendicular orientation relative to the cross-sectional plane intersecting both facets of the first pair of facets of the needle tip. Turning now to FIGS. 3 and 6, two cross-sectional planes are represented as Greek symbols $\alpha$ (alpha) corresponding to a "dorsal" cross-section, and $\beta$ (beta) corresponding to a "saggital" cross-section. In other words, the intact portion of the needle in the sampling notch region has a longitudinal axis (not shown) running along the exterior surface of the intact portion in general alignment with dorsal cross-sectional plane $\alpha$, which separates facets 6a and 6b. Referring now to FIG. 6, the open "face" of the sampling notch 8 is generally aligned with saggital cross-sectional plane β. Thus, when viewing facets 6a, 7a and 7b, a lateral or side view of sampling notch 8 results. The same lateral or side view of sampling notch 8 occurs when viewing facet 6b on the opposing side of the biopsy needle as shown in FIG. 7. The arrangement of the facets relative to the sampling notch results in the two side views (relative to the notch) as depicted in FIG. 4 and FIG. 7. This arrangement is important to reducing or minimizing deflection of the biopsy needle during the tissue penetration stages of the biopsy procedure, i.e., obtaining optimal results from the invention. In alternative but less preferred embodiments, the sampling notch can be oriented using more conventional positions, such as the same side of the main beveled surface or exact opposite side therefrom, as depicted in FIGS. 8A and B and 9A and B (referring to notch orientation only).

Another feature of the invention is that by virtue of the biopsy needle tip configuration and sampling notch orientation relative thereto, the distance from distal end of the sampling notch 8 to the needle tip 9 can be shortened relative to conventional biopsy needles. Although notch length can vary, the shortened notch-to-tip length reduces the extent of penetration damage to the surrounding tissue. Consequently, the invention affords yet another advantage of reducing patient trauma and increasing patient comfort.

Figure 10A:
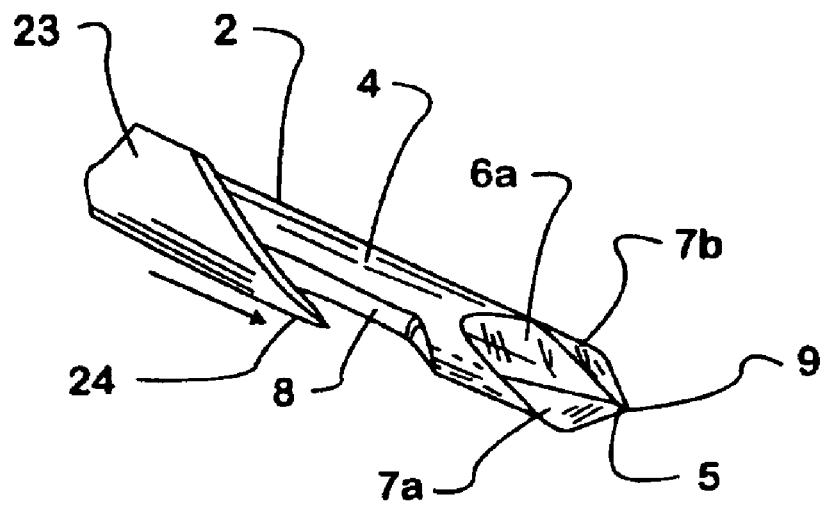
FIGS. 10A and 10B are angled side views of an outer cannula superimposed over a portion of the biopsy needle according to one embodiment of the invention.
Figure 10B:
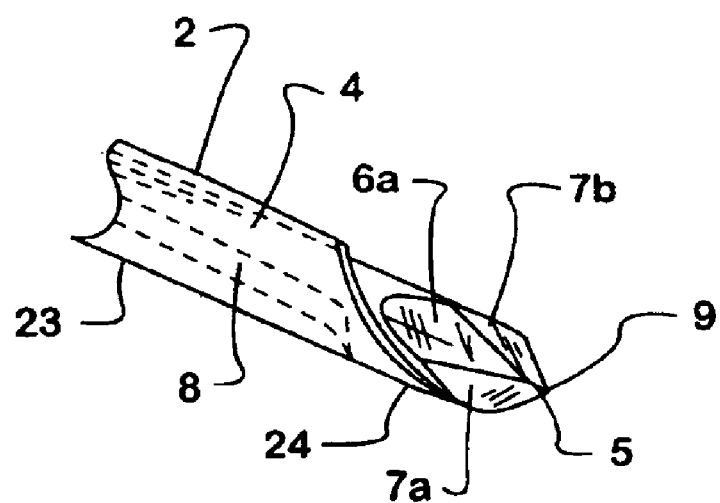

When the biopsy needle of the invention comprises the preferred sampling notch orientation together with the needle tip of the invention, further unnecessary damage to surrounding tissue can be avoided by the use of an outer cannula comprising distal tip which aligns with the tip geometry so as to permit complete superimposition of the outer cannula over the sampling notch while at the same time allowing for the use of minimized notch-to-tip length. In this embodiment of the invention, the biopsy device comprises an outer cannula comprising a sharp beveled end that coordinate with the needle tip geometry so as to permit advancement of said sharp beveled end of said outer cannula beyond the sampling notch of said needle and alongside the area of the needle exterior surface between said first pair of facets without extending beyond the sharp distal end of said needle. Referring now to FIGS. 10A and 10B, the distal portion of an outer cannula 23 is illustrated as having a sharp beveled end 24 terminating to a point. In FIG. 10A, the outer cannula 23 is shown in advancing state covering the sampling notch 8 and toward the needle tip. As seen in FIG. 10B, the sharp beveled end 24 of the outer cannula 23 completely covers the sampling notch 8 and, thusly, would completely sever the tissue sample from surrounding tissue. The outer cannula 23 is structured and aligned relative to the needle in such a manner as to permit advancement of the sharp beveled end 24 of the outer cannula 23 between facets 6a and 6b (not shown) of the needle tip. As a result of the coordinated combination of the outer cannula 23 structure and needle tip, the notch-to-tip length can be minimized while maintaining complete tissue severance. Accordingly, accurate sampling can be performed using reduced tip protrusion because the outer cannula can extend beyond the distal "heel" of the sampling notch.

The biopsy needle of the invention can be manufactured using conventional materials, techniques (such as grinding) and equipment readily available in the medical device field. The biopsy needle body can be composed of any rigid material adapted to maintain its structural integrity upon experiencing the physical forces typically associated with biopsy procedures. Suitable materials include, but are not limited to, polymeric and metallic materials. Examples of preferred metallic materials include stainless steel, such as stainless steel 304, and titanium. The distal tip configuration can be prepared using conventional grinding tools and equipment.

The biopsy needle of the invention can be a component of a rapid-firing biopsy device. The biopsy device can be of the automatic or semi-automatic type, and comprises an outer cannula and needle assembly, the needle being constructed in accordance with the invention. Examples of devices within which the biopsy needle of the invention can be used are described in Bauer U.S. Pat. No. 5,951,489, Bauer U.S. Pat. No. 5,916,175, Bauer U.S. Pat. No. 5,313,958, and Chu et al. U.S. Pat. No. 5,989,196, the entire text of each of which is incorporated herein by reference. In general, the components of such devices can include a handle, trigger mechanism, outer cannula and biopsy needle having a notch. Upon activation of the trigger mechanism, the needle is propelled forward in the distal direction at a high velocity such that the distal end of the needle extends beyond the distal end of the outer cannula and penetrates the tissue. The notch is exposed to the tissue and an amount of tissue encroaches into the notch. Upon advancement of the outer cannula over the needle and notch, the tissue is severed or pinched-off from the surrounding tissue and captured in the notch. The interior surface of the outer cannula contains the sample in the notch space and prevents the loss of the sample during removal of the outer cannula an needle assembly from the sampling site.

The biopsy needle according to the invention affords advantages to the operation of devices which employ advancement of a needle into soft materials, e.g., rapidly advancing biopsy needles. By virtue of its structure, the faceted tip of the needle facilitates penetration of the tissue by the needle, and interacts with the tissue and the encountered forces caused by its advancement in a manner which encourages the maintaining of the linear configuration of the needle during the advancement stage (e.g., "straight track"). The tip distributes the resulting forces and, in conjunction with the notch orientation relative to the tip, reduces the likelihood of bending or biasing the needle, i.e., deflection, during rapid tissue penetration. Consequently, the needle performs a cleaner, straighter penetration through the tissue, thereby reducing or minimizing the extent of trauma that would result from deviation from the straight track tissue penetration. This is especially important in circumstances wherein the needle is penetrating tissue of a very dense lesion, for example.

The invention is further illustrated by the following examples.

EXAMPLES

Figure 8B:
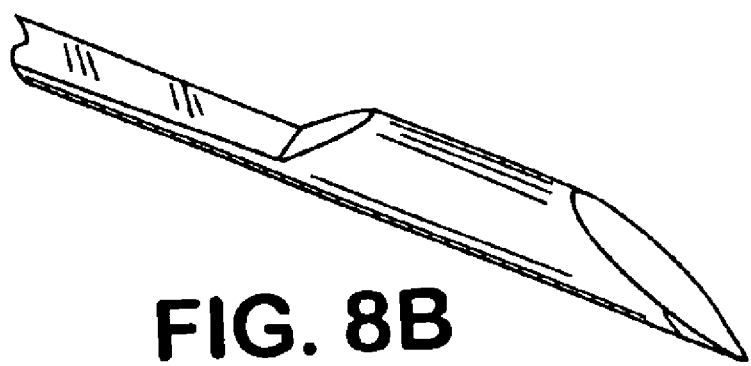

The prior art biopsy needles used in the following examples that were compared to the biopsy needle of the invention are depicted in FIGS. 8A and 8B ("Temno™ I") and FIGS. 9A and 9B ("Temno™ II"). As can be seen from the figures, both of these needle tips comprise a three-facet beveled tip. The sampling notch orientations differ, however, with the Temno™ I notch being on the same side as the faceted face of the tip and the Temno™ II notch being on the side opposite the faceted face of the tip. The biopsy needle of the invention, on the other hand, can comprise the notch facing laterally between the same side as the major facets and the opposite side thereof.

Example 1

Comparative Needle Sharpness

Figure 9A:
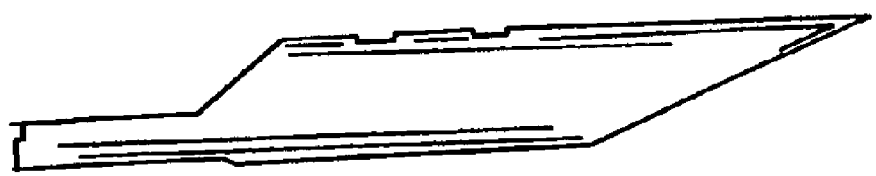
FIGS. 9A and 9B are a side view and angled side view, respectively, of the distal end of a prior art biopsy needle Temno™ II, to which the biopsy needle of the invention is compared in the examples.
Figure 9B:
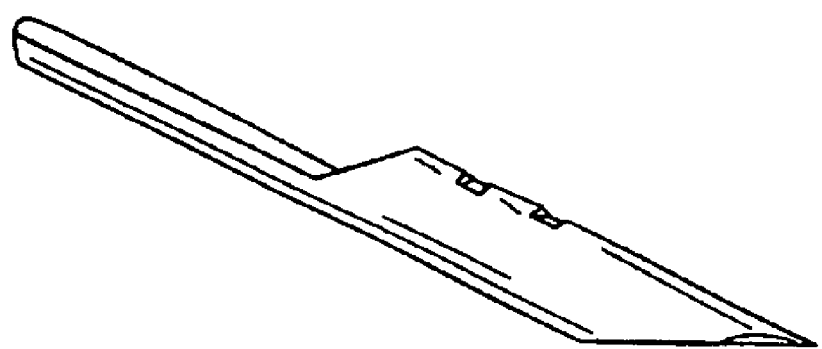

Needle sharpness was evaluated comparing the biopsy needle of the invention to Temno™ I (Prior Art FIGS. 8A and 8B) and Temno™ II (Prior Art FIGS. 9A and 9B). The Temno™ brand biopsy needles can be obtained from Cardinal Health, Inc., Waukegan, Ill.). Four sizes of each needle structure (the invention, Temno™ I and Temno™ II) were tested—14, 16, 18 and 20 gauge. Thirty (30) test needles of each gauge (14, 16, 18 and 20) and type (invention, Temno™ I, Temno™ II) were used. Each test needle punctured the film ten (10) times. Per test group, 300 data points were averaged (30 needles×10 punctures each). A total of twelve (12) test groups (4 gauges each of the invention, Temno™ I and Temno™ II).

Each test needle was placed into a chuck that held the needle, and the chuck and needle were then placed into a force transducer (force testing machine). The force testing machine was calibrated and attached to the computer/data recorder which processes the signals from the force transducer and records output. A polymeric film (0.008" gauge polyethylene film, 9"×12" sheet, ULINE S-7001) was stretched over a collar and locked into place to create a uniform, taut surface for puncture by the test needle. The chuck holding the needle was advanced into the film at a constant speed of 1100 mm/min. As the needle advanced through the film, the computer recorded the transducer output until the needle traveled to a predetermined amount. Once this amount has been reached, the force testing machine stopped and withdrew the needle from the film. The data was compiled using Microsoft™ Excel 2000™ (9.0.3821 FR-1) and Minitab™ Statistical Software V 13.32. The maximum force required for the needle to penetrate the test film was recorded and used to measure needle sharpness—a lower value indicating a shaper needle and a higher value indicating a duller needle.

The results are summarized in the following tables:

TABLE 1

Comparative Average Peak Insertion Force

Average Peak Insertion Force (lbf)

| Gauge | Temno ™ I | Temno ™ II | Invention |
|---|---|---|---|
| 14 | 0.558 | 0.403 | 0.376 |
| 16 | 0.438 | 0.268 | 0.202 |
| 18 | 0.335 | 0.326 | 0.274 |
| 20 | 0.231 | 0.222 | 0.237 |

TABLE 2

Comparative Percent Sharpness Difference

Percent Decrease in Insertion Force (Increase in Sharpness) (%)

| Gauge | Invention vs. Temno ™ I | Invention vs. Temno ™ II |
|---|---|---|
| 14 | 32.6 | 6.7 |
| 16 | 53.9 | 24.6 |
| 18 | 18.2 | 10.2 |
| 20 | 0 | 0 |

As can be seen from the above results, the biopsy needle of the invention requires less force to penetrate tissue, and is at least as sharp and up to about 54% sharper as compared to the tip geometry of prior art biopsy needles. Thus, the biopsy needle of the invention exhibits enhanced tissue penetration properties.

Example 2

Comparative Needle Tracking

Needle tracking was evaluated comparing the biopsy needle of the invention to Temno™ I (Prior Art FIGS. 8A and 8B) and Temno™ II (Prior Art FIGS. 9A and 9B). The Temno™ brand biopsy needles can be obtained from Cardinal Health, Inc., Waukegan, Ill.). Four sizes of each needle structure were tested—c14, 16, 18 and 20 gauge. Thirty (30) test needles of each gauge biopsy needle were tested, using one puncture per needle. Each test sample was introduced into tissue phantom (Computerized Imaging Reference System (CIRS)—Formulation 20 zerdine). This material simulates dense liver tissue and is recommended as a mimic of hard lesion inside healthy tissue simulations. Each needle was placed into the tissue phantom for the same distance, and the amount of deflection for each needle was measured using a comparator. The data was compiled using Microsoft™ Excel 2000™ (9.0.3821 FR-1) and Minitab™ Statistical Software V 13.32.

The results are summarized in the following tables:

TABLE 3

Comparative Amount of Deflection

Average Amount of Deflection (mm)

| Gauge | Temno ™ I | Temno ™ II | Invention |
|---|---|---|---|
| 14 | 1.291 | 1.002 | 0.188 |
| 16 | 1.642 | 1.601 | 0.377 |
| 18 | 2.044 | 2.380 | 1.367 |
| 20 | 1.918 | 1.947 | 0.341 |

TABLE 4

Comparative Percent Deflection Difference

Percent Decrease in Deflection (%)

| Gauge | Invention vs. Temno ™ I | Invention vs. Temno ™ II |
|---|---|---|
| 14 | 85.3 | 81.2 |
| 16 | 76.8 | 76.5 |
| 18 | 32.8 | 42.6 |
| 20 | 82.3 | 82.5 |

As can be seen from the above results, the biopsy needle of the invention tracks significantly better, from about 33 to about 85% straighter, in comparison to the prior art biopsy needles. Beveled tips on biopsy needles have a tendency to bias and deviate from a straight penetration track. Based on the above results, it can be seen that the biopsy needle of the invention reduces the tendency to bias during travel into tissue. Thus, there is less tendency of the biopsy needle of the invention to unnecessarily traumatize the tissue site during the procedure. Furthermore, the practitioner is afforded some assurance that the needle tip will reach the target tissue with precision thereby retrieving the desired sample.

Example 3

Comparative Notch-to-Needle Length

The biopsy needle of the invention permits the use of significantly shorter notch-to-needle length, thereby reducing the length of the needle tip required to penetrate and obtain the tissue sample. The tip length (notch-to-tip) for four gauge sizes—14, 16, 18 and 20—for each of the biopsy needles of the invention, Temno™ I (FIGS. 8A and 8B) and Temno™ II (FIGS. 9A and 9B)—were compared.

The results are summarized in the following tables:

TABLE 5

Comparative Tip Length

| | Nominal Tip Length (mm) | | |
|---|---|---|---|
| Gauge | Temno ™ I | Temno ™ II | Invention |
| 14 | 7.0 | 10.0 | 5.65 |
| 16 | 6.8 | 9.0 | 6.75 |
| 18 | 6.0 | 8.0 | 4.45 |
| 20 | 5.5 | 7.0 | 3.90 |

TABLE 6

Comparative Percent Tip Length Reduction

| | Percent Decrease in Tip Length (%) | |
|---|---|---|
| Gauge | Invention vs. Temno ™ I | Invention vs. Temno ™ II |
| 14 | 19.3 | 43.5 |
| 16 | 0.70 | 25.0 |
| 18 | 25.1 | 44.3 |
| 20 | 29.1 | 44.3 |

As can be seen from the above data, the biopsy needle of the invention contains a notch-to-needle length that is significantly shorter, even up to 29% shorter, than prior art devices Temno™ I and Temno™ II. Thus, the biopsy needle of the invention reduces the amount of longitudinal tissue damage needed to obtain the sample from the tissue site.

INDUSTRIAL APPLICABILITY

The invention is particularly useful as the penetrating or sample-obtaining component of a biopsy device which comprises mechanisms for rapid high velocity movement of a biopsy needle into soft tissue. When employed as a component of a biopsy device, the features of the inventive biopsy needle, such as the tip configuration, sampling notch orientation in relation thereto, and shorter notch-to-tip length, provide the user increased precision and accuracy, and afford the patient reduced trauma and greater comfort.

The invention has been described herein above with reference to various and specific preferred embodiments and techniques. It will be understood by one of ordinary skill, however, that reasonable modifications and variations of such embodiments and techniques can be made without significantly departing from either the spirit or scope of the invention as set forth in the following claims.

What is claimed is:

1. A biopsy needle for use in soft tissue sampling procedures comprising an elongate needle body having a longitudinal axis and sharp distal end having four facets, wherein each individual facet is substantially planar and said facets are arranged such that:

each of a first pair of facets is positioned on the opposite side of the needle from the other, and both of said substantially planar surfaces of the first pair facets are oriented in a converging direction toward the distal-most end of the needle end;

each of a second pair of facets is positioned such that each facet of said second pair is positioned between each of said first pair of facets, and both of the second pair of facets distally converge with one another so as to form a shared edge substantially in alignment with the longitudinal axis of the needle and said shared edge is positioned between distal-most points of each of said first pair of facets.

2. The biopsy needle according to claim 1 further comprising a sampling notch located proximal to the needle tip and comprises an intact portion with an open face.

3. The biopsy needle according to claim 2, wherein said open face comprises a surface having a generally perpendicular orientation relative to the cross-sectional plane intersecting both facets of the first pair of facets.

4. A biopsy device comprising an outer cannula and a biopsy needle assembly, a portion of said biopsy needle residing within said outer cannula and structured to move relative thereto, said biopsy needle comprising:

an elongated needle body having a longitudinal axis and sharp distal end having four facets, wherein each individual facet is substantially planar and said facets are arranged such that:

each of a first pair of facets is positioned on the opposite side of the needle from the other, and both of said substantially planar surfaces of the first pair facets are oriented in a converging direction toward the distal-most end of the needle end;

each of a second pair of facets is positioned such that each facet of said second pair is positioned between each of said first pair of facets, and both of the second pair of facets distally converge with one another so as to form a substantially in alignment with the longitudinal axis of the needle and said shared edge is positioned between distal-most points of each of said first pair of facets.

5. The biopsy device according to claim 4, wherein said biopsy needle further comprises a sampling notch located proximal to the needle tip and comprises an intact portion with an open face.

6. The biopsy device according to claim 5, wherein said open face comprises a surface having a generally perpendicular orientation relative to the cross-sectional plane intersecting both facets of the first pair of facets.

7. The biopsy device according to claim 6, wherein said outer cannula comprises a sharp beveled end that coordinates with the needle tip geometry so as to permit advancement of said sharp beveled end of said outer cannula beyond the sampling notch of said needle and alongside the area of the needle exterior surface between said first pair of facets without extending beyond the sharp distal end of said needle.

8. A biopsy needle comprising an elongated body, longitudinal axis, sharp distal end having four facets, and a sampling notch located proximal to said distal end, wherein each individual facet is substantially planar and said facets are arranged such that:

each of a first pair of facets is positioned on the opposite side of the needle from the other, and both of said substantially planar surfaces of the first pair facets are oriented in a converging direction toward the distal-most end of the needle end;

each of a second pair of facets is positioned such that each facet of said second pair of facets distally converge with one another so as to form a shared edge substantially in alignment with the longitudinal axis of the needle and said shared edge is positioned between distal-most points of each of said first pair facets;

and wherein said sampling notch comprises an intact portion with an open face comprising a surface having a generally perpendicular orientation relative to the cross-sectional plane intersecting both facets of the first pair of facets.

9. A needle for penetration of soft materials comprising an elongated needle body having a longitudinal axis and sharp distal end having four facets, wherein each individual facet is substantially planar and said facets are arranged such that:

each of a first pair of facets is positioned on the opposite side of the needle from the other, and both of said substantially planar surfaces of the first pair facets are oriented in a converging direction toward the distal-most end of the needle end;

each of a second pair of facets is positioned such that each facet of said second pair is positioned between each of said first pair of facets, and both of the second pair of facets distally converge with one another so as to form a shared edge substantially in alignment with the longitudinal axis of the needle and said shared edge is positioned between distal-most points of each of said first pair of facets.

* * * * *